(12) United States Patent
Skubitz

(10) Patent No.: US 10,206,707 B2
(45) Date of Patent: Feb. 19, 2019

(54) UTILIZING MULTIPLE LINKS TO ACHIEVE A DESIRED TOOL DEFLECTION ANGLE WHEN CLEARING AN EPIDURAL SPACE

(71) Applicant: MEDTRONIC, INC., Minneapolis, MN (US)

(72) Inventor: Sean P. Skubitz, Forest Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 396 days.

(21) Appl. No.: 14/885,053

(22) Filed: Oct. 16, 2015

(65) Prior Publication Data

US 2016/0038171 A1 Feb. 11, 2016

Related U.S. Application Data

(62) Division of application No. 13/752,597, filed on Jan. 29, 2013, now Pat. No. 9,161,762.

(60) Provisional application No. 61/618,662, filed on Mar. 30, 2012.

(51) Int. Cl.

| | | |
|---|---|---|
| A61B 19/00 | (2006.01) |
| A61B 17/3205 | (2006.01) |
| A61B 17/16 | (2006.01) |
| A61B 17/32 | (2006.01) |
| A61B 17/34 | (2006.01) |
| A61B 17/29 | (2006.01) |
| A61B 90/50 | (2016.01) |

(52) U.S. Cl.
CPC .......... *A61B 17/3205* (2013.01); *A61B 17/16* (2013.01); *A61B 17/32* (2013.01); *A61B 17/320016* (2013.01); *A61B 17/3401* (2013.01); *A61B 2017/2904* (2013.01); *A61B 2017/2905* (2013.01); *A61B 2017/320044* (2013.01); *A61B 2090/508* (2016.02)

(58) Field of Classification Search
CPC . A61B 17/16; A61B 17/32; A61B 17/320016; A61B 17/3401; A61B 2017/2904; A61B 2017/2905; A61B 2017/320044
See application file for complete search history.

(56) References Cited

U.S. PATENT DOCUMENTS 5,448,989 A * 9/1995 Heckele ............... A61B 1/0055
600/104
5,916,147 A * 6/1999 Boury ............... A61M 25/0147
600/139

(Continued)

*Primary Examiner* — Gregory Anderson
(74) *Attorney, Agent, or Firm* — Withers & Keys, LLC

(57) ABSTRACT

An epidural space is cleared of fat and scar tissue in preparation for implantation of a medical lead by utilizing a clearing tool. The clearing tool has multiple links that allow the creation of a deflection angle. A wire passes through the links and once the links are positioned with the desired deflection angle, tension is placed on the wire to lock the links into the current position. The clearing tool is inserted through a window into the epidural space, and once the tension is applied to the wire, the clearing tool becomes rigid to allow advancement of the clearing tool within the epidural space. The clearing tool is then removed from the epidural space, and the medical lead is inserted through the window and cleared epidural space until reaching the target site.

8 Claims, 7 Drawing Sheets

(56) References Cited

U.S. PATENT DOCUMENTS

2003/0125725 A1* 7/2003 Woodard ........... A61B 18/1492
606/41
2008/0161809 A1* 7/2008 Schmitz ............. A61B 17/1604
606/79

* cited by examiner

UTILIZING MULTIPLE LINKS TO ACHIEVE A DESIRED TOOL DEFLECTION ANGLE WHEN CLEARING AN EPIDURAL SPACE

TECHNICAL FIELD

Embodiments are related to the implantation of medical leads used for stimulation within the epidural space. More particularly, embodiments relate to methods and tools that utilize multiple links to achieve a desired tool deflection angle when clearing the epidural space in preparation for implantation of a medical lead.

BACKGROUND

Various medical conditions may call for therapeutic electrical stimulation within the epidural space of the spine. Therefore, medical leads capable of delivering stimulation signals are implanted within the epidural space. In some cases, it may be necessary to clear the epidural space as well as the entryway to the epidural space of fatty tissue, scar tissue, and the like in order to provide for easier ingress of the medical lead. This is particularly true for paddle leads that are implanted through a surgical procedure due to the relatively wide distal paddle on the medical lead.

Conventionally, a rigid plastic tool or a soft plastic tool is inserted into the epidural space through a window created within the vertebral bone and associated ligaments. However, the rigid plastic tool presents multiple issues. A first issue is that the rigid plastic provides minimal deflection when entering the epidural space at an angle through the window and thus creates a potential pressure point along the dura of the spinal cord which can cause discomfort and potential paralysis. Another issue is that once in the epidural space, the rigid plastic tool often has less than adequate clearing ability. The soft plastic also presents multiple issues. Once inside the epidural space the soft plastic may deflect in an undesired direction. Additionally, the soft plastic may not have the stiffness to track in the ideal direction. This is particularly true as the width and length of the paddle continues to grow with newer versions of paddle leads where the increased paddle width increases the likelihood of snagging the blockages within the epidural space. Furthermore, the rigid plastic tool with minimal deflection cannot enter at a shallow enough angle to allow for adequate insertion distance needed to reach and clear the target stimulation site.

SUMMARY

Embodiments address issues such as these and others by providing multiple links within a clearing tool that are used to create a desired deflection angle for insertion and clearing within the epidural space. The links allow the deflection angle to be adjusted and locked by having a wire passing through the links that can be under tension to lock the deflection angle and released from tension when setting the deflection angle.

Embodiments provide a method of clearing an epidural space using a clearing tool that has at least two links. The method involves creating slack between the at least two links and establishing a desired angle between the at least two links. The method further involves tightening contact between the at least two links to lock the links at the desired angle as well as inserting the clearing tool through a window into the epidural space. Additionally, the method involves continuing to insert the clearing tool with the at least two links locked at the desired angle until a distal tip of the clearing tool at least reaches a target site and then removing the clearing tool through the window.

Embodiments provide a method of implanting a medical lead within an epidural space that involves creating slack between at least two links of a cleaning tool. The method further involves establishing a desired angle between the at least two links and tightening contact between the at least two links to lock the links at the desired angle. Additionally, the method involves inserting the clearing tool through a window into the epidural space and continuing to insert the clearing tool with the at least two links locked at the desired angle until a distal tip of the clearing tool at least reaches a target site. The method also involves removing the clearing tool through the window and after removing the clearing tool, inserting the medical lead through the window and into the epidural space.

Embodiments provide a clearing tool for preparing an epidural space for implantation of a medical lead. The clearing tool includes a handle with a biasing mechanism, the biasing mechanism being opposable. The clearing tool further includes a wire attached to the biasing mechanism such that the biasing mechanism creates tension on the wire and releases tension on the wire when a bias of the biasing mechanism is being opposed. Additionally, the clearing tool includes at least two links with the wire passing through each of the at least two links such that tension on the wire forces the at least two links into contact and includes a distal tip affixed to a most distal link.

DETAILED DESCRIPTION

Embodiments provide for methods and tools for clearing the epidural space in preparation for implantation of a medical lead within the epidural space. The clearing tool includes multiple links that can be used to form a desired deflection angle used when inserting the tool and clearing the epidural space. The multiple links may be forced into secure contact to lock the deflection angle and may be allowed to separate to release the deflection angle. When released, a different deflection angle may be established which may then be subsequently locked in place by again forcing secure contact of the links.

Figure 1:
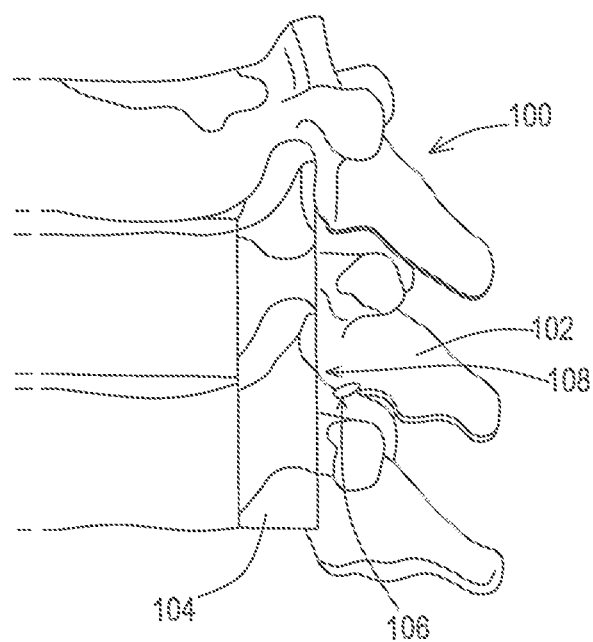
FIG. 1 shows a spine with a window created to access the epidural space.

FIGS. 1-4 illustrate a method of clearing the epidural space and implanting the medical lead within the cleared epidural space. FIG. 1 shows a spinal region 100 of a patient where the implantation of a medical lead is desired. Prior to clearing the epidural space 108, a surgeon has created a window 106 in the spinal region 100 in the conventional manner by cutting through any vertebral bone and ligaments that block entryway to the epidural space 108 that occurs between the dura 104 of the spinal cord and the inner surface of the vertebral bone 102.

Figure 2:
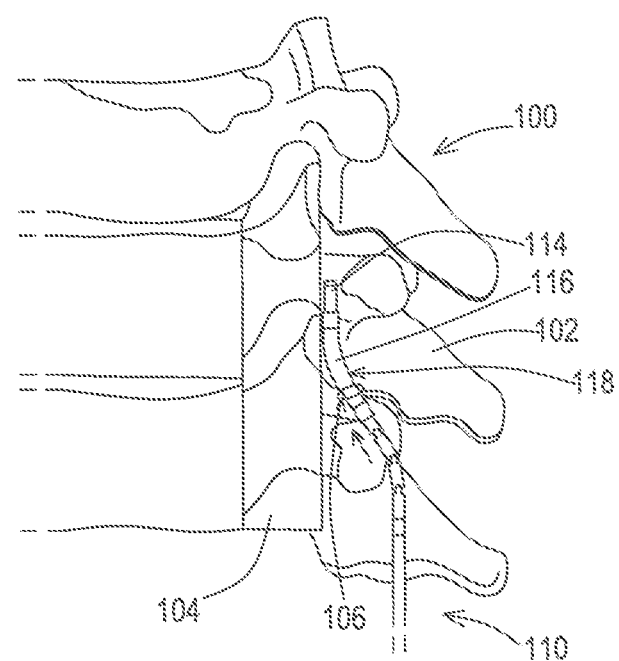
FIG. 2 shows an example of a clearing tool with multiple links being inserted into the epidural space while in a locked state.

FIG. 2 shows the insertion of the clearing tool 110 into the epidural space 108 by passing through the window 106 until the distal end of the clearing tool 110 becomes directed axially along the dura 104. The clearing tool 110 includes a series of end-to-end links 112 creating a series of articulation points. In this example, a sleeve 116 is provided to further protect the dura 104 from direct contact with any individual link 112 present within a deflection area 118. The deflection of the clearing tool 110 achieves alignment in the axial dimension of the dura 104. This deflection is the result of angles established and secured between links 112 present in the deflection area 118. The angles are created by the clinician manipulating the links 112 while in a released state and are than secured by a locked state. The creation of the deflection angle in the deflection area 118 ensures that the clearing tool 110 does not create undue pressure on the dura 104 when entering the epidural space 108.

Additional angles may also be created between other links 112 of the clearing tool 110. For example, links closer to a handle of the clearing tool 110 may create an angle that is opposite that of the deflection area 118 thereby creating a compound bend over the length of the clearing tool 110 so as to allow for movement of the handle of the clearing tool 110 in a direction parallel to the axial dimension of the spinal cord. Such an opposite angle and the relative positioning of the handle of the clearing tool 110 are discussed in more detail below in relation to FIG. 5A.

As an alternative to establishing the angle prior to insertion through the window 106, the clearing tool 110 may be left in a released state during insertion so as to allow the links 112 to achieve a naturally induced deflection angle. Then, upon the distal tip 114 being fully inserted and aligned with the axial dimension of the spinal cord, the clearing tool 110 may be transitioned to the locked state to lock the deflection angle and create rigidity among the links 112 to allow for additional insertion and clearing of the epidural space 108.

The clearing tool 110 including each of the links 112 as well as the handle discussed below may be constructed of various materials such as acetal, polypropylene, polyethylene, or nylon (polyamide). The sleeve 116 may be made of a flexible, elastic material such as silicone rubber that can fit relatively tightly over the links 112 so as not to slide on the links 112 during insertion. To aid the clearing process, the links 112 and/or sleeve 116 of the clearing tool 110 may also be made radiopaque by including materials such as barium sulfate, and/or tungsten so as to be visible during fluoroscopy.

Figure 3:
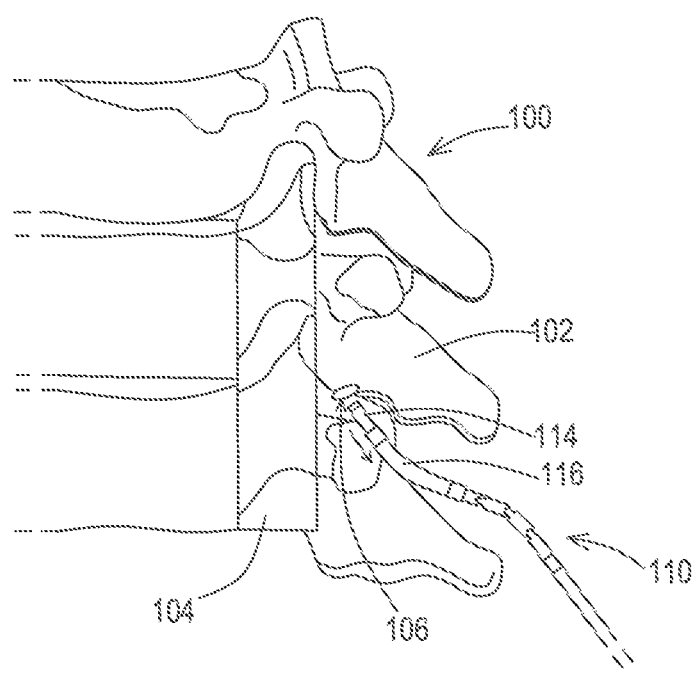
FIG. 3 shows the clearing tool in the locked state being removed from the epidural space.

Once the distal tip 114 has been advanced within the epidural space 108 to the target site, the clearing tool 110 may be retracted back through the window 106. The retraction of the clearing tool 110 is shown in FIG. 3. While the clearing tool 110 is being retracted, the links 112 of the clearing tool 110 may be transitioned to the released position to provide flexibility and the ability to freely deflect as needed for removal within the epidural space 108 in proximity to the window 106. The clearing tool 110 is directed out through the window 106 while the deflection area 118 continues to avoid undue pressure on the dura 104.

Figure 4:
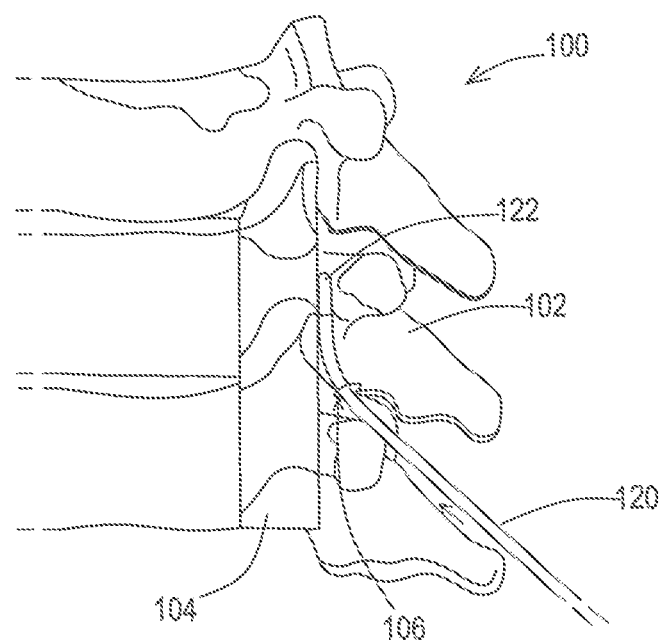
FIG. 4 shows the insertion of a medical lead into the cleared epidural space.

Once the clearing tool 114 has been removed from the spinal region 100, the medical lead 120 is then inserted through the window 106 and into the epidural space 108 as shown in FIG. 4. The medical lead 120 continues to be inserted until a distal end such as a paddle 122 of the medical lead 120 reaches the target stimulation site along the axial dimension of the dura 104. Afterward, the medical lead 120 is connected to a medical device that delivers the electrical stimulation signals that are output through electrodes in the distal end of the medical lead 120. As shown in FIG. 4, the body of the medical lead 120 may exceed that of the links 112 and sleeve 116 of the clearing tool 110, but the width of the distal tip 114 of the tool 110 has cleared the epidural space 108 so that the additional width of the medical lead 120 and the distal end 122 are not blocked during ingress by obstructions.

Figure 5A:
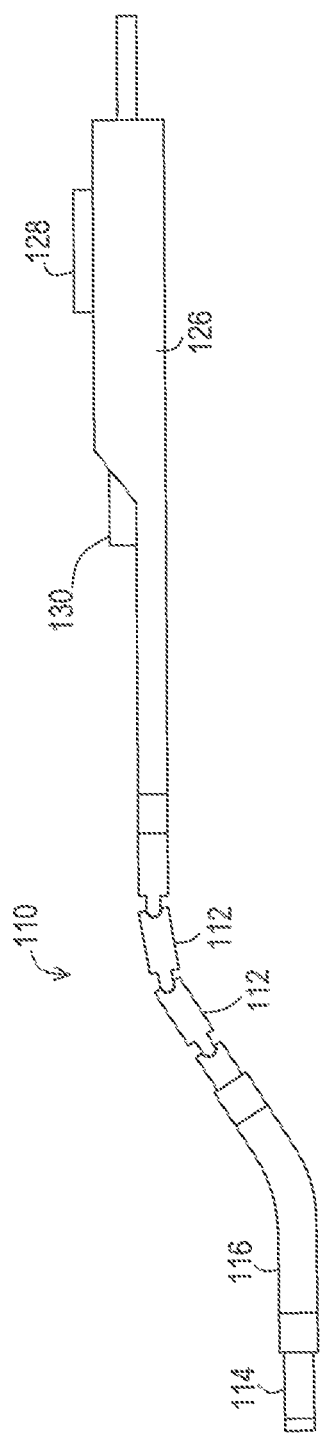
FIG. 5A shows a side view of an example of a clearing tool with multiple links in the locked state.

FIG. 5A shows a side view of the clearing tool 110 where multiple deflections have been established prior to insertion into the epidural space. The most distal links 112 which are present beneath the sleeve 116 are angled relative to adjacent links to create a deflection suitable for the distal end to enter the epidural space. The most proximal links 112 are angled oppositely relative to adjacent links as compared to angle between the most distal links to create a deflection that aligns the handle 126 with the axial dimension of the spinal cord. Thus, while inserting the distal end of the clearing tool 110 into the epidural space, a slight rotation of the proximal end in relation to the distal end of the handle 126 toward the spine to achieve alignment to the axial dimension of the spinal cord effectively aims the distal tip 114 parallel to the axial dimension of the spinal cord as well. Therefore, the advancement of the distal tip 114 during insertion of the clearing tool 110 while rotating the handle 126 as prescribed further avoids undue pressure on the dura 104.

The clearing tool 110 further includes a slider 128 that can be manipulated to establish the locked or released states of the links 112. The slider 128 includes guide posts 130 that retain the slider 128 within the handle 126 as the slider 128 is being moved in the proximal or distal directions. The top view of FIGS. 5B and 5C further show the relationship of the slider 128 and guideposts 130 to the handle 126 in both the locked state in FIG. 5B and the released state in FIG. 5C.

Figure 5B:
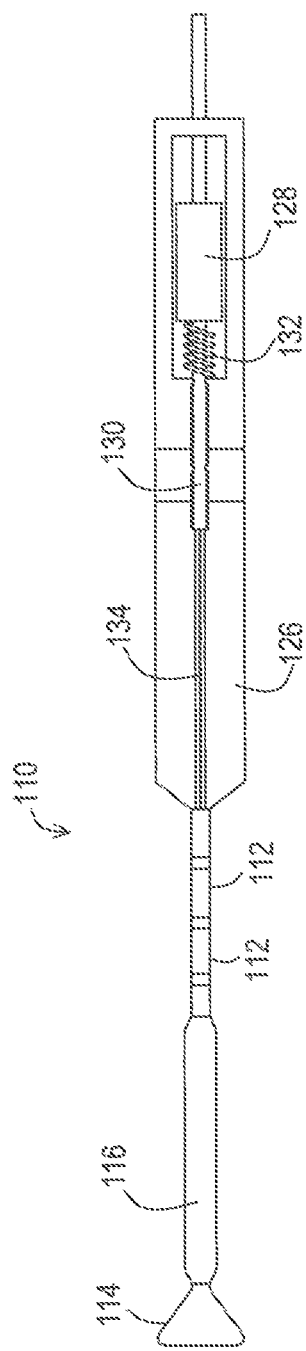
FIG. 5B shows a top view of the example of the clearing tool with multiple links in the locked state.
Figure 5C:
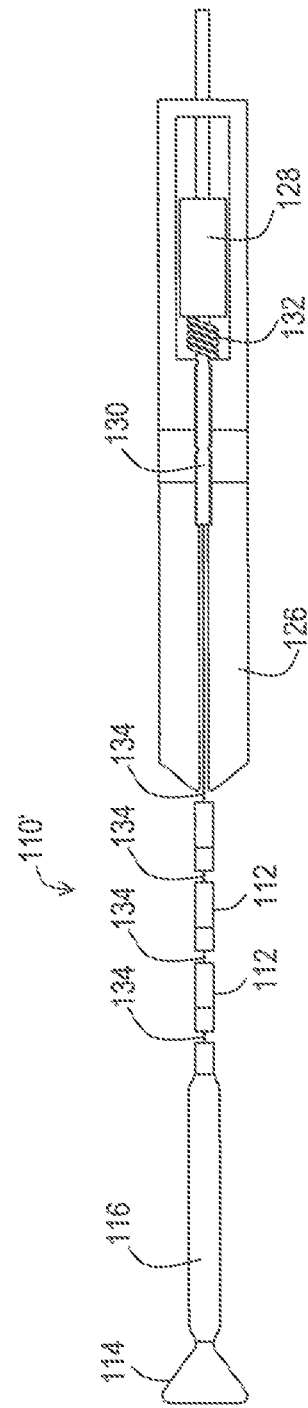
FIG. 5C shows a top view of the example of the clearing tool with multiple links in the released state.

In FIG. 5B, the locked state is achieved by a bias being applied to the slider 128 by a biasing mechanism such as the spring 132. While the biasing mechanism is shown as a coil spring 132, other biasing mechanisms are possible such as leaf springs. In this example, the spring 132 is present about the guidepost 130 of the slider 128 and abuts the handle 126 on one end and the slider 128 on the other. The spring 132 of this example biases the slider 128 in the proximal direction to impose the locked state upon the links 112 by creating tension on a wire 134. The proximal end of the wire 134 is attached to the slider 128 and/or guidepost 130 while the distal end of the wire 134 is attached to a most distal link 112 or the distal tip 114. As shown in FIG. 5C, a clinician applies force to the slider 128 in the distal direction to decrease the tension on the wire 134 and thereby impose the released state on the links 112, creating slack between each of the links 112 so that each is free to rotate several degrees relative to adjacent links 112.

In this particular example of FIGS. 5A-5C, when in the released state the links 112 are configured to achieve angles relative to adjacent links within a single geometric plane, namely the plane perpendicular to the back of the patient and parallel with the axial dimension of the spine. However, in this example the links 112 are maintained in a linear arrangement in the geometric plane of the back of the patient to avoid the links 112 from diverting laterally from the axial dimension of the spine. This is achieved by having links 112 with a concave end and a convex end such that a concave end of one link 112 engages a convex end of an adjacent link 112 that restricts relative movement to the single geometric plane.

Figure 6A:
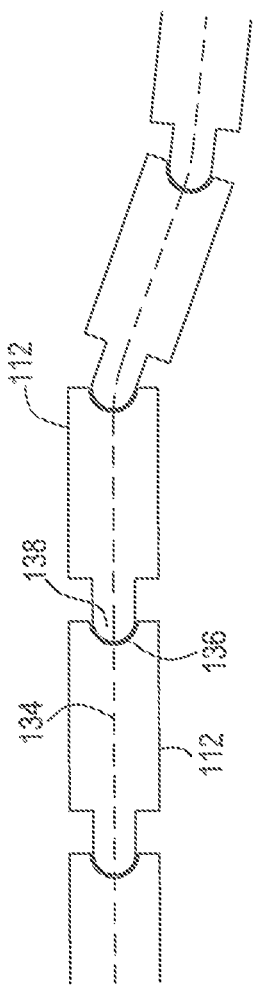
FIG. 6A shows an enlarged side view of multiple links of the clearing tool in the locked state.
Figure 6B:
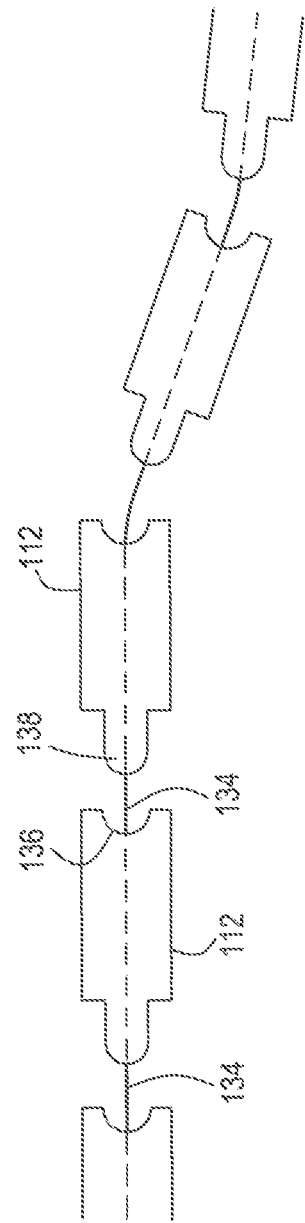
FIG. 6B shows an enlarged side view of multiple links of the clearing tool in the released state.

The engagement of a convex end with a concave end as in FIG. 5A is also shown in the enlarged view of the links 112 in FIGS. 6A and 6B. In this example, the distal end of each link 112 is convex while the proximal end is concave. However, it will be appreciated that the configuration may be reversed with the distal end being concave and the proximal end being convex to achieve the same articulation points.

Furthermore, it will be appreciated that there may be applications where it is desirable to create deflections in other geometric planes than the plane shown in FIGS. 5A-5C, 6A, and 6B. For instance, side entry procedures may benefit from deflection lateral to the axial dimension of the spine in addition to deflection in the plane shown in FIG. 5A. In such cases, embodiments of the clearing tool 110 may instead have ball and socket engagements between links 112 that allow for more degrees of freedom of movement, and hence an articulation in any desired geometric plane.

FIGS. 6A and 6B further illustrate the wire 134 used to hold the links 112 together and to impose the locked and released states. The wire 134 passes through a hole within each link 112 that extends from the proximal end to the distal end. When the wire 134 is under tension by the slider 128 as in FIG. 6A, the links 112 are brought into tight contact with one another that prevents further movement due to stiction between the engaged links 112. When tension on the wire 134 is decreased or removed altogether as in FIG. 6B, the tight contact between the links 112 is removed to create slack between the links 112 that allows the links 112 freedom of movement relative to one another.

The wire 134 may be a flexible single strand or may be flexible yet cabled, braided, and the like to increase tensile strength. Additionally, the wire 134 may be constructed of various biocompatible materials. For instance, in one embodiment the wire 134 is stainless steel. In another embodiment, the wire 134 is constructed of polyester.

While embodiments have been particularly shown and described, it will be understood by those skilled in the art that various other changes in the form and details may be made therein without departing from the spirit and scope of the invention.

What is claimed is:

1. A clearing tool for preparing an epidural space for implantation of a medical lead, comprising:
    a handle with a biasing mechanism, the biasing mechanism being opposable;
    a wire attached to the biasing mechanism such that the biasing mechanism creates tension on the wire and releases tension on the wire when a bias of the biasing mechanism is being opposed;
    at least two links with the wire passing through each of the at least two links such that tension on the wire forces the at least two links into contact; and
    a distal tip affixed to a most distal link, the distal tip having a proximal end and a distal end and the distal tip being wider at the distalmost end than at the proximal end.

2. The clearing tool of claim 1, wherein the biasing mechanism comprises:
    a slider movably engaged with the handle, the wire being coupled to the slider; and
    a spring abutting the handle and the slider, the spring biasing the slider proximally relative to the handle to apply the tension to the wire.

3. The clearing tool of claim 1, wherein each of the at least two links comprise one end that is concave and an opposite end that is convex such that a concave end of one link engages a convex end of an adjacent link.

4. The clearing tool of claim 1, further comprising a sleeve wrapped around the at least two links.

5. A clearing tool for preparing an epidural space for implantation of a medical lead, comprising:
    a handle with a biasing mechanism, the biasing mechanism being opposable;
    a wire attached to the biasing mechanism such that the biasing mechanism creates tension on the wire and releases tension on the wire when a bias of the biasing mechanism is being opposed;
    at least two links with the wire passing through each of the at least two links such that the at least two links are not in contact with each other when the biasing mechanism releases tension on the wire and the at least two links are in contact with each other when the biasing mechanism creates tension on the wire; and
    a distal tip affixed to a most distal link.

6. The clearing tool of claim 5, wherein the biasing mechanism comprises:
    a slider movably engaged with the handle, the wire being coupled to the slider; and
    a spring abutting the handle and the slider, the spring biasing the slider proximally relative to the handle to apply the tension to the wire.

7. The clearing tool of claim 5, wherein each of the at least two links comprise one end that is concave and an opposite end that is convex such that a concave end of one link engages a convex end of an adjacent link.

8. The clearing tool of claim 5, further comprising a sleeve wrapped around the at least two links.

* * * * *